United States Patent [19]

Franetzki et al.

[11] 4,082,088
[45] Apr. 4, 1978

[54] APPARATUS FOR DETERMINATION OF RESPIRATORY PASSAGEWAY RESISTANCE

[75] Inventors: Manfred Franetzki, Erlangen; Volker Korn, Nuremberg; Karl Prestele, Erlangen, all of Germany

[73] Assignee: Siemens Aktiengesellschaft, Berlin & Munich, Germany

[21] Appl. No.: 748,385

[22] Filed: Dec. 7, 1976

Related U.S. Application Data

[63] Continuation-in-part of Ser. No. 559,872, Mar. 19, 1975, abandoned.

[30] Foreign Application Priority Data

Mar. 22, 1974 Germany .............................. 2414019
Nov. 28, 1974 France .................. 74 38993

[51] Int. Cl.² ............................................... A61B 5/08
[52] U.S. Cl. ................................................ 128/2.08
[58] Field of Search .............. 128/2.08, 2.07, DIG. 29

[56] References Cited

U.S. PATENT DOCUMENTS

| | | | |
|---|---|---|---|
| 3,036,569 | 5/1962 | Clements et al. ................... | 128/2.08 |
| 3,713,436 | 1/1973 | Hardway ............................ | 128/2.08 |
| 3,857,385 | 12/1974 | Hampl ................................ | 128/2.08 |

FOREIGN PATENT DOCUMENTS

| | | | |
|---|---|---|---|
| 1,913,337 | 10/1969 | Germany .......................... | 128/2.08 |
| 850,750 | 10/1960 | United Kingdom ................ | 128/2.08 |

OTHER PUBLICATIONS

*Journ. of Applied Physiology,* vol. 8, pp. 587–594, 1956.
*Medical Instrumentation,* vol. 9, No. 1, Jan.–Feb. 1975, pp. 3–10.

*Primary Examiner*—Kyle L. Howell
*Attorney, Agent, or Firm*—Hill, Gross, Van Santen, Steadman, Chiara & Simpson

[57] ABSTRACT

An apparatus for the determination of the respiratory passageway resistance, including a breathing tube which incorporates a flow resistance and a pulse generator for subjecting the breath flow to higher frequency pressure or, respectively, current pulsations, as well as a pressure gauge for measuring the pressure in the breathing tube. The pressure gauge is constituted of an alternating pressure gauge coordinated with the pulsating frequency of a pulse generator. As alternating pressure gauge there may be utilized a common mechanical-electrical transducer which, for detection of the alternating pressure, has an electrical frequency filter connected thereto.

14 Claims, 4 Drawing Figures

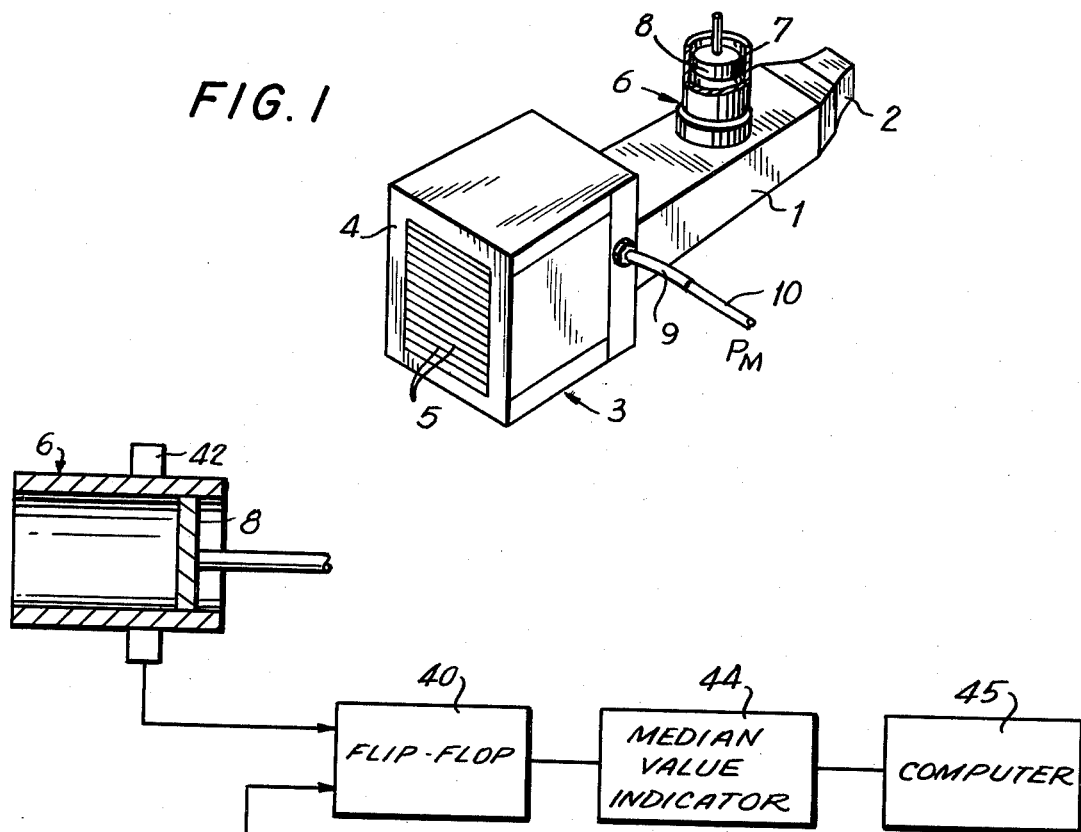

APPARATUS FOR DETERMINATION OF RESPIRATORY PASSAGEWAY RESISTANCE

CROSS-REFERENCE TO RELATED APPLICATION

The present application is a continuation-in-part of the parent application, Ser. No. 559,872 filed Mar. 19, 1975 now abandoned.

FIELD OF THE INVENTION

The present invention relates to an apparatus for the determination of the respiratory passageway resistance, including a breathing tube which incorporates a flow resistance and a pulse generator for subjecting the breath flow to higher frequency pressure or, respectively, current pulsations, as well as a pressure gauge for measuring the pressure in the breathing tube.

DISCUSSION OF THE PRIOR ART

A known apparatus contains a T-shaped static pressure head tube whose end communicating with atmosphere is closed off by means of an adjustable iris diaphragm forming the flow resistance. A piston pump is connected to the base portion of the T-shaped tube, which superimposes pressure oscillations onto the breath flow in the breathing tube at a frequency of approximately 3 Hz. The measuring principle is based on the concept that during breathing through the tube, the iris diaphragm is displaced for so long until a differential pressure gauge connected to the tube at both sides of the base portion indicates a zero reading. The flow resistance which is represented by the iris diaphragm serves hereby as the direct measure for the respiratory passageway resistance. In another apparatus known in the art, in lieu of the iris diaphragm, there is utilized a fixed resistance $Z_a$. By means of a differential pressure gauge which is connected to the tube, the internal pressure P of the tube is measured in comparison with the external pressure, and through a flow gauge located in the pumping path, meaning, in the base portion of the tube, there is measured the flow $\dot{V}$ produced by the piston pump. From the measured pressure and flow values, as well as the known resistance value $Z_a$ of the fixed flow resistance, there then is calculated the breathing passageway resistance $Z_b$ in accordance with the relationship $1/Z_b = \dot{V}/P - 1/Z_a$.

The breathing or respiratory passageway resistances which are obtainable pursuant to the known measuring principles are, however, not sufficiently precise.

SUMMARY OF THE INVENTION

Accordingly, it is an object of the present invention to provide an apparatus of the above-mentioned type by means of which the respiratory passageway resistance may essentially be obtained in a more exact and precise manner.

The foregoing object is inventively achieved in that the pressure gauge is constituted of an alternating pressure gauge coordinated with the pulsating frequency of a pulse generator.

Prior to the present invention investigations were carried out as to why the known measuring principles did not deliver sufficiently exact measuring results. As a first important reason therefor it had been found that the known measuring principles did not encompass, as is inherently required, the respiratory passageway resistance as the real component of an alternating current-respiratory passageway impedance separate of capacitive and/or inductive resistance components (which play a not insignificant role on the basis of the superimposed relatively high-frequency pressure-or-flow changes in the flow path play). More frequently, obtained as the "respiratory passageway resistance" is always a conglomerate constituted of the two resistance components. A second reason for the occurrence of the measuring errors possibly may lie in that the known above-mentioned measuring methods demand relatively high pulsating amplitudes (piston displacement for the piston pump of approximately 50 cm$^3$). Hereby, the cheeks and other soft portions of the mouth and trachea are excited into vibrations to an excessive measure so as to, on the one hand, produce signal deformations and-/on the other hand, bring into effect short-circuiting capacitances. Further, as experience has indicated, the probed person reacts physically and psychologically to the excessively strong pulsations and, as a result, breathes unnaturally.

In the present invention, operation may be effected at low pressure, respectively, flow or current pulsations. The danger that the mouth or trachea portions of the patient will vibrate therewith, or that the patient will unnaturally react to these vibrations, is thus extensively eliminated. Furthermore, there is obtained the advantage that with the inventive alternating current measurement the quite complex respiratory passageway resistance allows itself to be exactly divided into the actual real component, an alternating current resistance, and into the imaginary component which is assembled from the capacitive and/or inductive components.

When consideration is given that in the equivalent-circuit diagram, with respect to pulsating inflow $\dot{v}$, the flow resistance $R_O$ and the respiratory passageway resistance $R_{aw}$ are connected in parallel, then from this parallel circuit diagram there is immediately obtained the following relationship for the mouth pressure $P_M$:

$$P_M = \frac{R_{aw} \cdot R_o}{R_{aw} + R_o} \cdot \dot{v}$$

From the foregoing, after recalculation, there is again obtained the respiratory passageway resistance $$R_{aw} = \frac{P_M \cdot R_o}{\dot{v} \cdot R_o - P_M}$$

In the case of sinusoidal pulsations, this resistance value automatically corresponds to the sought-after respiratory passageway resistance, when there is inserted for $\dot{v}$, respectively, the measured alternating pressure $P_M$, presently the sine amplitude $\hat{v}$, respectively, $\hat{P}_M$.

Inasmuch as $\hat{v}$ may be fixedly set through the sinusoidal displacement of the pulse generator (for example, the piston lift when using a piston pump), and thereby preselected the base resistance value $R_O$ of the flow resistance and consequently known, the respiratory passageway resistance $R_{aw}$ may be obtained through a single alternating pressure measurement ahead of the mouth. A comparative pressure measurement is only required when, additionally, there must also be determined the breath flow.

The calculation of the respiratory passageway resistance $R_{aw}$ pursuant to the above-mentioned relationship may be carried out, for example, by means of a slide rule, or graphically. However, there may be preferably provided an electronic computer circuit, which includes correspondingly selected multiplier-divider-and subtracting elements for the automatic computation of the respiratory passageway resistance.

As an alternating pressure gauge there may be utilized a common mechanical-electrical transducer which, for detection of the alternating pressure, has an electrical frequency filter connected thereto, preferably a band-pass filter, synchronized to the pulsating frequency. It is, however, suitable that there be employed as the alternating pressure gauge a pressure sensitive resistor which is responsive to alternating pressures at the pulsating frequency, as for example, a microphone.

BRIEF DESCRIPTION OF THE DRAWINGS

Further advantages and details of the invention may now be ascertained from the following description of an exemplary embodiment, thereof, taken in conjunction with the accompanying drawings; in which:

FIG. 1 illustrates in a perspective view the mechanical construction of an apparatus according to the invention, in which the breathing tube is subjected to preferably sinusoidal pressure or, respectively, current pulsations;

FIG. 2 illustrates a schematic circuit diagram of the associated electrical measuring and calculating circuit;

DETAILED DESCRIPTION

Figure 3:
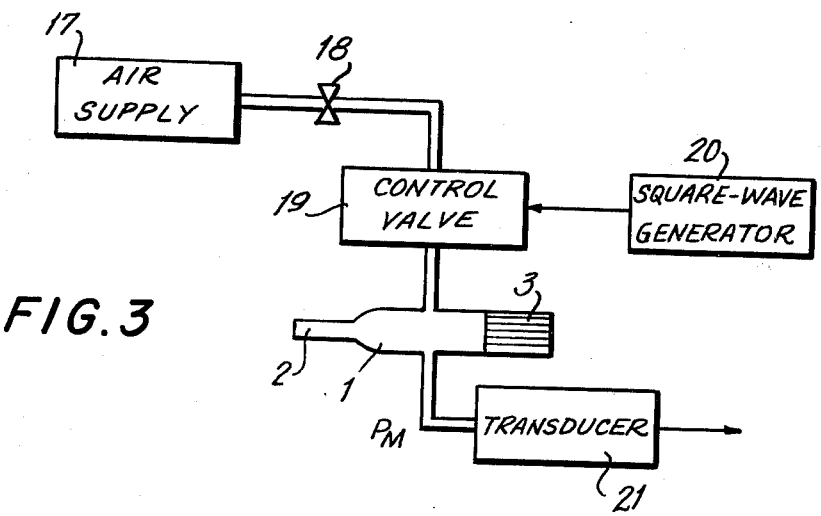
FIG. 3 shows a diagrammatic construction of an apparatus pursuant to the invention, in which the breathing tube is subjected to preferably square-wave pressure or, respectively, current pulsations.

Referring now in detail to the drawings, FIG. 1 illustrates a breathing tube 1 whose mouth-sided end is provided with a mouthpiece 2. The other end of the breathing tube 1 is closed off by means of a flow-independent flow resistance 3, the latter of which is constructed, for example, in the type of a lamellar receptor. The resistance 3 (generally corresponding to the lamellar receptor as disclosed in German Laid-Open patent specification No. 2,044,101) consists of a housing 4 whose inner chamber is divided into a plurality of narrow (approximately 0.2 mm wide) parallel flow chambers by means of thin foils 5 which, for example, are formed of polyvinyl chloride. The flow receiving surface of the receptor 3 is selected so that the resistance value $R_o$ of the flow resistance preferably lies within the range of approximately 1 to 5 mbar/l/s.

Further communicating with the breathing tube 1 is a piston pump 6 having a cylinder 7 and a piston 8. The piston pump 6 is driven by a suitable electro-motor (not shown) in a manner so that the piston 8 is sinusoidally articulated within cylinder 7. Due to the sinusoidal piston articulation, the pressure or, respectively, respiratory flow in the breathing tube 1 is subjected to sinusoidal pressure or, respectively, current or flow pulsations. The sine frequency of the piston pump 6 lies within the range of between about 5 and 20 Hz, and preferably at 12 Hz. The lift of the sine variations should thereby consist of a maximum of ±10% of the amplitudes of the basic breathing pressure or, respectively, the basic breath flow in breathing tube 1. The piston pump 6 may also be located separated from the breathing tube, for example, in a signal processing apparatus, and may be connected with the tube through a pneumatic conduit.

At the apparatus according to FIG. 1, there is measured in the operating condition thereof (the patient breathes at the moving piston 8 of the piston pump through the mouthpiece 2 into the breathing tube 1 and lamellar receptor 3) the total mouth pressure $P_M$ through a single pressure outlet connector 9 having a pneumatic connector conduit 10, which communicates with the connector location intermediate the breathing tube 1 and the lamellar receptor 3.

The pressure $P_M$, pursuant to FIG. 2, is conveyed to a mechanical-electrical transducer 11 which, in this instance, preferably is formed of a pressure sensitive transistor or of a piezo-microphone responsive to the alternating pressures at the pulsation frequency. The transducer 11 with frequency filter 11a may also be directly located on the breathing tube. The alternating components $p_M$ detected by the transducer 11 are then subsequently transmitted to an electronic computer circuit for calculation of the respiratory passageway resistance. This computer circuit consists hereby of a first multiplier element 12 for forming the product between the known sine amplitude of the alternating current or flow pulsations $\hat{v}$ in the breathing tube 1, as well as the basic resistance value $R_o$ of the lamellar receptor 3. Furthermore, there is provided a subtracting element 13 (operational amplifier) for forming the difference $\hat{v} \cdot R_o - \hat{p}_M$, as well as a second multiplier element 14 for multiplication of the pressure signal $\hat{p}_M$ with the basic resistance value $R_o$. Connected to the subtracting element 13, as well as to the second multiplier element 14, there is additionally a dividing element 15 which calculates from the output signals of the elements 13 and respectively 14, the respiratory passageway resistance signal $$R_{aw} = \frac{\hat{p}_M R_o}{\hat{v} R_o - \hat{p}_M}$$

This output signal is then finally transmitted to an indicating or registration apparatus for indication or registration of the respiratory passageway resistance value $R_{aw}$.

The indicating or registration apparatus 16, while dispensing with any linear information, may be directly calibrated into resistance units. The non-linearity of the indication or information is thereby not disadvantageous, inasmuch as the largest sensitivity, meaning the largest scale spread, lies at small values of $R_{aw}$ and the physiological reproductability of large values (such as over 10 mbar/l/s) is in any event questionable. At full-scale reading of the instrument, namely $p_M = \hat{v} \cdot R_o$, the respiratory passageway resistance rises towards infinity, whereby there is concurrently provided a good calibration standard (closing off the mouth side of the resistance gauge and adjusting the instrument to full-scale reading).

Should during the respiratory passageway resistance detection, there be considered the phase displacement $\beta$ between the flow or current pulsations $\hat{v}$ and the inspected pressure pulsations $p_M$ (normally very small), then in addition to the pressure amplitude of $p_M$, this phase must also be measured. That type of phase measurement, for example, may be undertaken when, respectively at the passing through zero of the detected alternating pressure $p_M$ by means of indicator 41 a bistable trigger or flip-flop 40 is displaced from one to the other stable condition thereof, and presently set back through a trigger impulse, which is correlated in a timewise fixed manner with the current or flow superposition (for example, through the signal of a light barrier 42,43 which is located on the piston 8 of the piston pump). The light barrier has a light transmitter 42 and light receiver 43. The light beam between these elements 42,43 is interrupted by piston 8, when this piston reaches the zero position corresponding to $\dot{v} = 0$. Pulses resulting from the interruption of the light beam between elements 42 and 43 reset flip-flop 40. The median value (compensating component) of the output voltage of the flip-flop which is detected, for example, through a low-pass filter 44 or the like, then becomes a direct measure for the phase angle.

If the thus measured phase angle between $\dot{v}$ and $p_M$ is designated by $\alpha$, there then exists the following interrelationship between the amount Z and the phase angle $\beta$ of the complex respiratory passageway resistance $R_{aw}$.

$$R_{aw} = Z \cdot e^{j\beta}$$

wherein $$Z = R_o \frac{p}{\sqrt{1 - p^2 + 2P \cos \alpha}}$$

$$\beta = \arcsin \frac{Z}{p R_o} \sin \alpha$$

Hereby p is the with $|\dot{v}|R_o$ normalized pressure $|P_M|$:

$$p = \frac{|p_M|}{|\dot{v}| R_o} \quad 0 \leq p \leq 1$$

The actual component of the complex respiratory passageway resistance is then presently calculated into $$Re (R_{aw}) = Z \cdot \cos \beta.$$

The calculation of this actual component may be specially effected through suitable electronic calculating elements 45. Just as well, this actual component may be read off from a diagram or chart which represents the actual component in dependence upon the phase angle $\beta$ and the normalized pressure p.

In lieu of the sinusoidal superimposed pressure or, respectively, current pulsations, there further may also be used square wave-shaped pulsations.

The square wave frequency is to be thereby so adjusted that, on the one hand, build-up sequences are reduced more rapidly than in the half-period duration and, on the other hand, the time constants which are formed through the lung capacity (compliance) and respiratory passageway resistance remained large as compared to a half period duration.

The pressure $p_M$ is then preferably measured by means of the so-caled "sample-and-hold technique," presently at the end of each half-wave, and may then subsequently be calculated in accordance with the previously produced relationship:

$$R_{aw} = \frac{p_M \cdot R_o}{\dot{v} \cdot R_o - p_M}.$$

In FIG. 3 of the drawings, the breathing tube is again designated by reference numeral 1, as well as the mouthpiece being designated with reference numeral 2. The breathing tube is again closed off with a lamellar receptor 3, as described in connection with FIG. 1. In lieu of the piston pump, however, there is now connected to the breathing tube 1 an air supply receptacle 17 having air at a definite above atmospheric or overpressure through a reduction valve 18, as well as a pilot or control valve 19. The control valve 19 is then alternately opened and again closed in beat with the desired square-wave frequency of the output impules of a square-wave generator 20. The breath flow in the breathing tube 1 is then subjected to square-wave shaped pressure or, respectively, current pulsations. Provided as the transducer for the pressure $p_M$ is a normal mechanical-electrical transducer 21.

Figure 4:
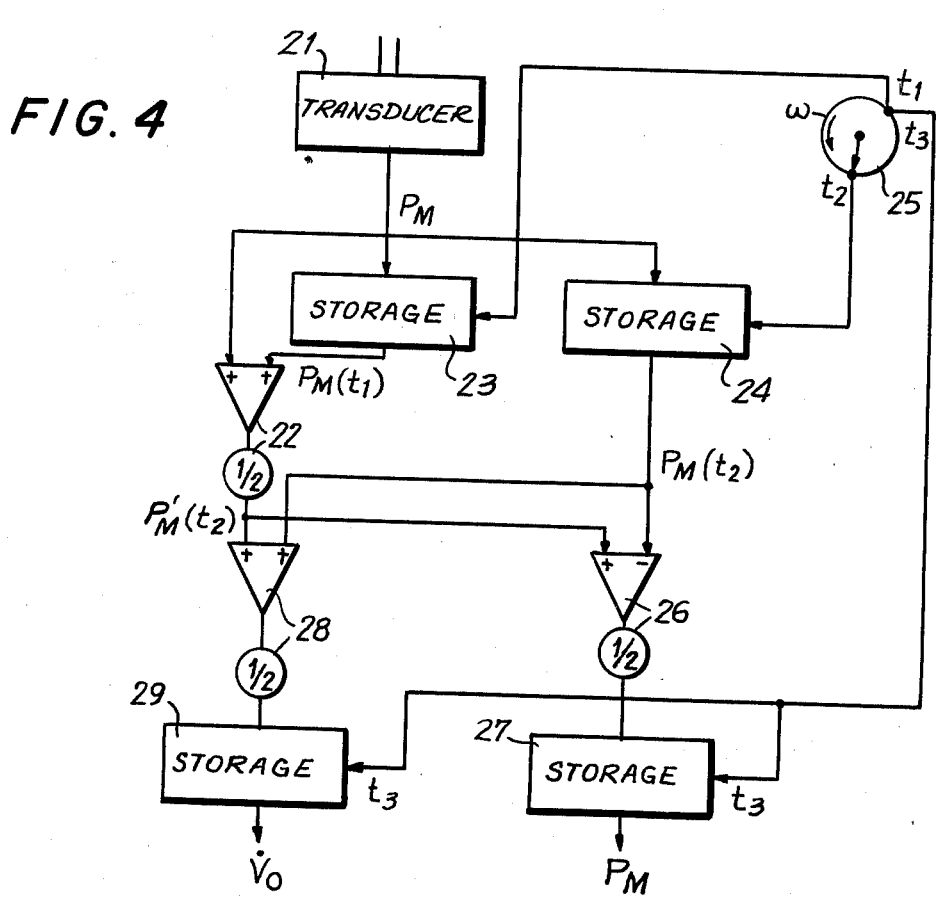
FIG. 4 is an associated circuit arrangement for obtaining the alternating pressure $P_M$, as well as the respiratory flow $\dot{V}_o$ at square-wave pressure or current pulsations pursuant to the so-called "sample-and-hold" technique.

According to FIG. 4, the pressure signal $P_M$, which corresponds to the total mouth pressure, is permanently transmitted to an adding element 22. Furthermore, two storage elements 23 and 24 are connected to the transducer 21, which retain the instantaneous values of the pressure $P_M$ at times $t_1 = t_3$ and $t_2$. The times $t_1 = t_3$ and $t_2$ are hereby predetermined by means of a timer 25 actuated in the square-wave pulse beat $\omega$. The times presently correspond to the time intervals between two switching sequences of the control valvee 19, whereby these time periods are located within such impulse sections of the square-wave impulses, whereby build-up sequences are presently reduced, meaning preferably within the impulse sections shortly preceding the switching time points.

If hereby $t_1$ is considered as the beginning and $t_3$ as the end of each impulse oscillation (whereby $t_3$ = the beginning $t_1$ of a new impulse oscillation), then at the output of the adding element 22 there is currently provided in $t_3$ the arithmetic means of $P_M(t_1)$ and $P_M(t_3)$, meaning the "high" mouth pressure $P_M'(t_2)$ calculated back to $t_2$. The sought alternating pressure component $P_M$ is then obtained from the difference between $P_M(t_2)$ and $P_M'(t_2)$. For forming this difference there is provided a differential former 26 having a storage element 27 connected thereto for the storage of the presently measured pressure value $P_M$.

The adder 28 in contrast therewith forms the arithmetic mean of $P_M'(t_2)$ and $P_M(t_2)$. This mean value corresponds to the median mouth pressure at time $t_2$. The medium mouth pressure may similarly be stored in a storage element 29 and, upon requirement, after corresponding calibration be called upon as the measure for the breath flow $\dot{V}_o$.

The alternating or variable pressure $P_M$ which is obtained in this manner may then be calculated through a computer circuit according to FIG. 2 in the previously described manner in conjunction with $\dot{v}$ and $R_o$ into the respiratory passageway resistance $R_{aw}$.

In lieu of the evaluation through the "sample-and-hold" technique, at square wave-shaped current superposition there may naturally also be correspondingly evaluated the sinusoidal current or flow superposition, namely when the particular basic sine wave of the alternating pressure is used as the basis for the calculations. This basic sine wave may easily be determined by means of a transducer having a thereto connected band-pass filter which is set to the basic wave frequency.

While there has been shown what is considered to be the preferred embodiment of the invention, it will be obvious that modifications may be made which come within the scope of the disclosure of the specification.

What is claimed is:

1. In an apparatus for determining respiratory passageway resistance, including a breathing tube for conveying a breath flow; a flow resistance in said breathing tube, a pulse generator for subjecting said breath flow to high frequencied pressure and, respectively, flow pulsations; and pressure measuring means comprising a mechanical-electrical transducer for measuring the pressure in said breathing tube, the improvement comprising: an electrical frequency filter connected to said mechanical-electrical transducer for detecting the alternating pressure in said breath flow received by said transducer, said frequency filter being correlated to said pulsating frequency of said pulse generator; and an electronic computer circuit having multiplying, dividing and subtracting elements being connected to the output of said frequency filter, said computer circuit mathematically computing the respiratory passageway resistance $R_{aw}$ from the measured alternating pressure $P_M$, the predetermined resistace value $R_o$ of the flow resistance, and the predetermined flow pulsations $\dot{v}$ of the pulse generator, in accordance with the relationship $$R_{aw} = \frac{P_M R_o}{\dot{v} R_o - P_M}.$$

2. An apparatus as claimed in claim 1, wherein said transducer comprises a pressure-sensitive transistor responsive to alternating pressures at the pulsating frequency.

3. An apparatus as claimed in claim 1, wherein said transducer comprises a microphone.

4. An apparatus as claimed in claim 1, said pulse generator generating pulsations having a basic frequency in the range of substantially 3 to 20 Hz, said frequency filter being set to said basic frequency.

5. An apparatus as claimed in claim 4, said basic frequency being 12 Hz.

6. An apparatus as claimed in claim 1, said flow resistance comprising a lamellar receptor for closing off said breathing tube.

7. An apparatus as claimed in claim 1, comprising a phase measurement element being connected to said alternating pressure measuring means and to said pulse generator for detecting the phase angle $\alpha$ between the alternating pressure and the flow superposition.

8. An apparatus as claimed in claim 7, said phase measurement element comprising a bistable flip-flop, said flip-flop being displaced from one stable condition thereof into the other stable condition upon zero-through passage of the alternating pressure, and being returned to the initial condition thereof responsive to a signal correlated with the flow superposition so as to form the measure for the phase angle for the medium value of the output voltage of the flip-flop.

9. An apparatus as claimed in claim 8, said pulse generator comprising a piston pump having a reciprocable piston, said correlated signal being provided by a light barrier on said piston.

10. An apparatus as claimed in claim 8, including a low-pass filter for detecting said medium value of the output voltage of said flip-flop.

11. An apparatus as claimed in claim 7, comprising an electrical computer circuit means for calculating the actual portion of the respiratory passageway resistance $R_{aw}$ pursuant to the relationship.

$$Re (R_{aw} = Z \cos \beta )$$

wherein $$Z = R_o \frac{p}{\sqrt{1 - p^2 + 2p \cos \alpha}}$$

$$\beta = \arcsin \left( \frac{-z}{p R_o} \sin \alpha \right)$$

with $p = \frac{|p_M|}{|\dot{v}| R_o}$

12. An apparatus as claimed in claim 1, comprising a sample-and-hold evaluation circuit for determining the amplitude of the alternating pressure at non-sinusoidal flow superposition, including first and second storage elements for storing the breathing pressure values ascertained by said pressure gauge means at predetermined successive timepoints during a pulsating period; an adding means for determining the mean values of the pressures at the end of one timepoint and commencement of a successive pulsating period, said mean value corresponding to a high mouth pressure calculated to an intermediate timepoint; and a subtracting element for forming the difference $$p_M + P_M{'}(t_2) - P_M(t_2).$$

13. An apparatus as claimed in claim 12, comprising a second adding means for determining the arithmetic means value of $P_M{'}(t_2)$ and $P_M(t_2)$ as the measure for the breath flow.

14. An apparatus as claimed in claim 13, said first and second adding elements each having a storage element associated therewith for the values $p_M$ and, respectively $\dot{V}_o$.

* * * * *